United States Patent [19]

Tamm et al.

[11] Patent Number: 4,534,646
[45] Date of Patent: Aug. 13, 1985

[54] DEVICE FOR ATOMIZING A SAMPLE IN FLAMELESS ATOMIC ABSORPTION SPECTROSCOPY

[75] Inventors: Rolf G. A. Tamm, Salem; Toma Tomoff, Uberlingen, both of Fed. Rep. of Germany

[73] Assignee: Bodenseewerk Perkin-Elmer & Co., GmbH, Uberlingen, Fed. Rep. of Germany

[21] Appl. No.: 483,989

[22] Filed: Apr. 11, 1983

[30] Foreign Application Priority Data

May 8, 1982 [DE] Fed. Rep. of Germany ....... 3217417

[51] Int. Cl.$^3$ ............................................. G01N 21/74
[52] U.S. Cl. ................................... 356/312; 356/244
[58] Field of Search ........................ 356/312, 244, 246

[56] References Cited

U.S. PATENT DOCUMENTS

| | | | |
|---|---|---|---|
| 4,111,553 | 9/1978 | Garnys | 356/312 X |
| 4,204,770 | 5/1980 | Tomoff | 356/312 |
| 4,396,287 | 8/1983 | Hildebrand et al. | 356/312 X |
| 4,406,540 | 9/1983 | Grossman et al. | 356/312 X |
| 4,443,105 | 4/1984 | Huber et al. | 356/312 |

FOREIGN PATENT DOCUMENTS 0053349 6/1982 European Pat. Off. .
3009794 9/1981 Fed. Rep. of Germany .

Primary Examiner—F. L. Evans
Attorney, Agent, or Firm—E. T. Grimes; J. D. Crane

[57] ABSTRACT

A lamella-shaped sample carrier is attached to a tubular carriage and is movable into a graphite tube of a graphite tube cuvette from the end fact below the measuring light beam of an atomic absorption spectrophotometer. The carriage with the sample carrier is movable between an inner position, a dosing position and an outer position. The sample carrier is electrically heated in any position by means of busses. Drying and ashing of the sample take place outside the graphite tube. The graphite tube is then heated to atomizing temperature, while the sample carrier is in its outer position. Subsequently, the sample carrier is advanced into the inner position and heated itself. Thus, rapid atomization of the sample is achieved.

6 Claims, 7 Drawing Figures

DEVICE FOR ATOMIZING A SAMPLE IN FLAMELESS ATOMIC ABSORPTION SPECTROSCOPY

BACKGROUND OF THE INVENTION

The present invention generally relates to a device for atomizing a sample in flameless atomic absorption spectroscopy and, in particular, relates to a device including means for heating the electrodes thereof regardless of the position thereof.

A conventional device is the subject matter of European patent application No. 81 109 879. Therein is described a method and device for introducing a sample into a graphite tube in flameless atomic absorption spectroscopy, in which device a lamella- or crucible-shaped sample carrier is introduced into the graphite tube from the end face in axial direction. Drying and ashing of the sample is effected outside the graphite tube. The sample carrier may be heated indirectly by radiation or directly by electric current being passed therethrough. Different types of sample carriers are disclosed.

SUMMARY OF THE INVENTION

It is one object of the present invention to provide such a device wherein heating of the sample carrier by electric current is possible in any position of the sample carrier.

This object is achieved, at least in part, by a device wherein the guide of the carriage include busses engaged by sliding contacts of the carriage which in turn are electrically connected to terminals of the electrically conducting sample carrier such that a heating current may be passed through the sample carrier in any position of the carriage.

Other objects and advantages will become apparent to those skilled in the art from the following specification read in conjunction with the drawing attached hereto and the appended claims.

BRIEF DESCRIPTION OF THE DRAWING

One embodiment of the invention is described hereinbelow in greater detail with reference to the accompanying drawing, which is not drawn to scale and in which.

DETAILED DESCRIPTION OF THE INVENTION

Figure 1:
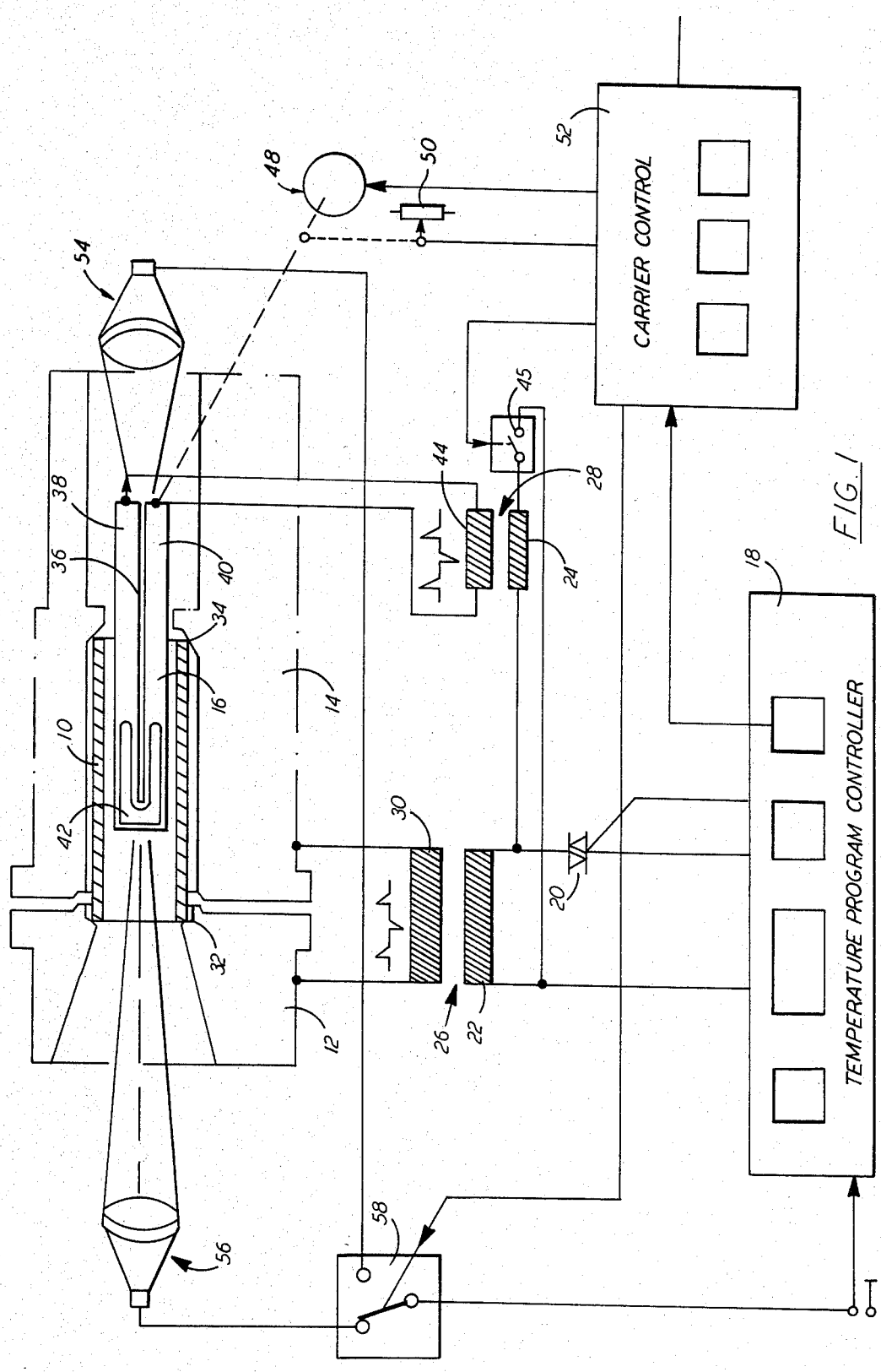
FIG. 1 shows schematically a device for atomizing a sample in flameless atomic absorption spectroscopy.

A graphite tube 10, generally indicated at 10 in the drawing, is mounted between graphite electrodes 12 and 14, the graphite electrode 14 extending over approximately the entire length around the graphite tube 10. The graphite electrodes 12 and 14 are preferably annular having a central aperture such that a measuring light beam of an atomic absorption spectrophotometer may pass through the graphite electrodes and through the graphite tube 10 in a longitudinal direction. A lamella-shaped sample carrier 16 is movable in longitudinal direction of the graphite tube 10 below the measuring light beam in a manner, more fully described hereinafter, such that it may be introduced into the graphite tube 10 from the end face, as illustrated in FIG. 1, or may be pulled out of the graphite tube. A power supply contains a program control 18 for the temperature. The program control 18 regulates the current through the primary windings 22 and 24 connected in parallel of a graphite tube transformer 26 and a sample carrier transformer 28 by means of a triac 20. The ends of the secondary winding 30 of the graphite tube transformer 26 are connected to the two electrodes 12 and 14. The graphite tube transformer 26 thus generates a heating current through the electrode 12, the left contact face 32 between the electrode 12 and the graphite tube 10, the right contact face 34 between the graphite tube 10 and the electrode 14 and finally the electrode 14. The sample carrier 16 includes a slot 36 extending from one end along the center line approximately up to the other end such that a generally U-shaped form having two legs 38 and 40 is obtained. A U-shaped cavity 42 for receiving the sample is formed in the base of the "U". The two legs 38 and 40 are connected to the ends of the secondary winding 44 of the sample carrier transformer 28 in a manner still to be described. A switch 45 is connected in series with the primary winding 24 of the sample carrier transformer 28.

The sample carrier 16 is adjustable along the longitudinal direction by means of a servomotor 48 in a manner described hereinafter. The position of the sample carrier 16 is detected by a position sensor in the form of a potentiometer 50. The potentiometer 50 supplies a position signal to a sample carrier control 52.

Figure 2:
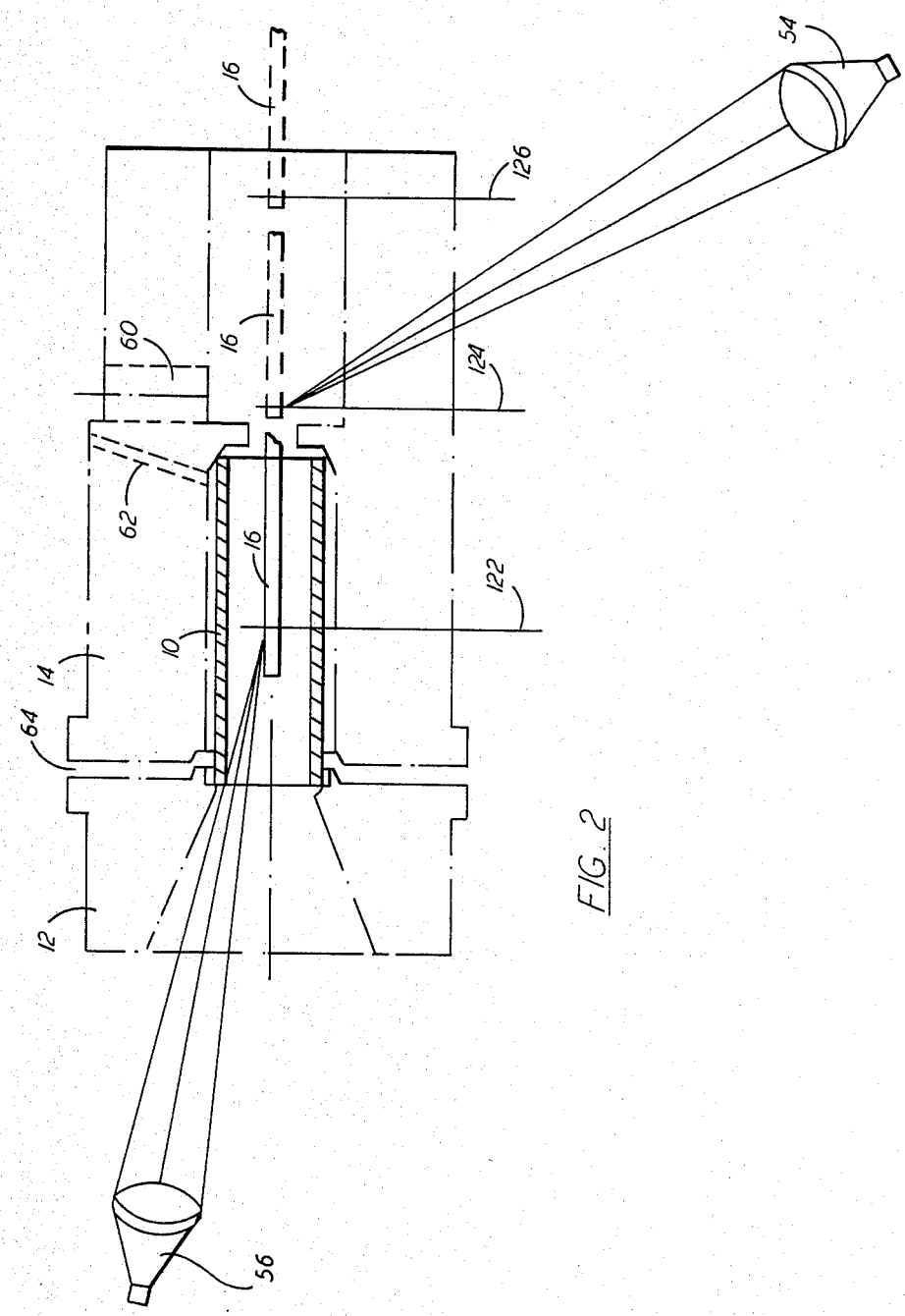
FIG. 2 illustrates the temperature measurement in the device of FIG. 1.

The temperature of the sample carrier is pyrometrically monitored by two sensors 54 and 56. A first pyrometric sensor 54 is directed upon the sample carrier 16 in its position outside the graphite tube 10. Referring specifically to FIG. 2, the first pyrometric sensor 54 is transversely directed towards the lower side of the sample carrier 16. A second pyrometric sensor 56 is disposed laterally with respect to the measuring light beam and is directed from the left end face of the graphite tube 10, as viewed in FIG. 2, transversely into the inside of the graphite tube 10. The temperature signals of the sensors 54 and 56 are supplied to the program generator 18 of the power supply as actual value signals of a temperature program control. To this end, alternately the first or the second sensor 54 or 56 can be connected to the power supply by means of a sensor selector switch 58 controlled by the sample carrier control 52.

As can be seen from FIG. 2, an inner gas flow passes through the aperture of the electrode 12 and through the inside of the graphite tube 10 to a dosing aperture 60 formed in the electrode 14. An outer gas flow passes through a bore 62 of the electrode 14 to the annular space between graphite tube 10 and electrode 14 and through this annular space to a gap 64 between the electrodes 12 and 14, where the outer gas flow emerges into atmosphere. Another outer gas flow enters the bore of the electrode 14 from the right hand side, as viewed in FIG. 2, and flows around the sample carrier 16, when it is retracted from the graphite tube 10.

Figure 3:
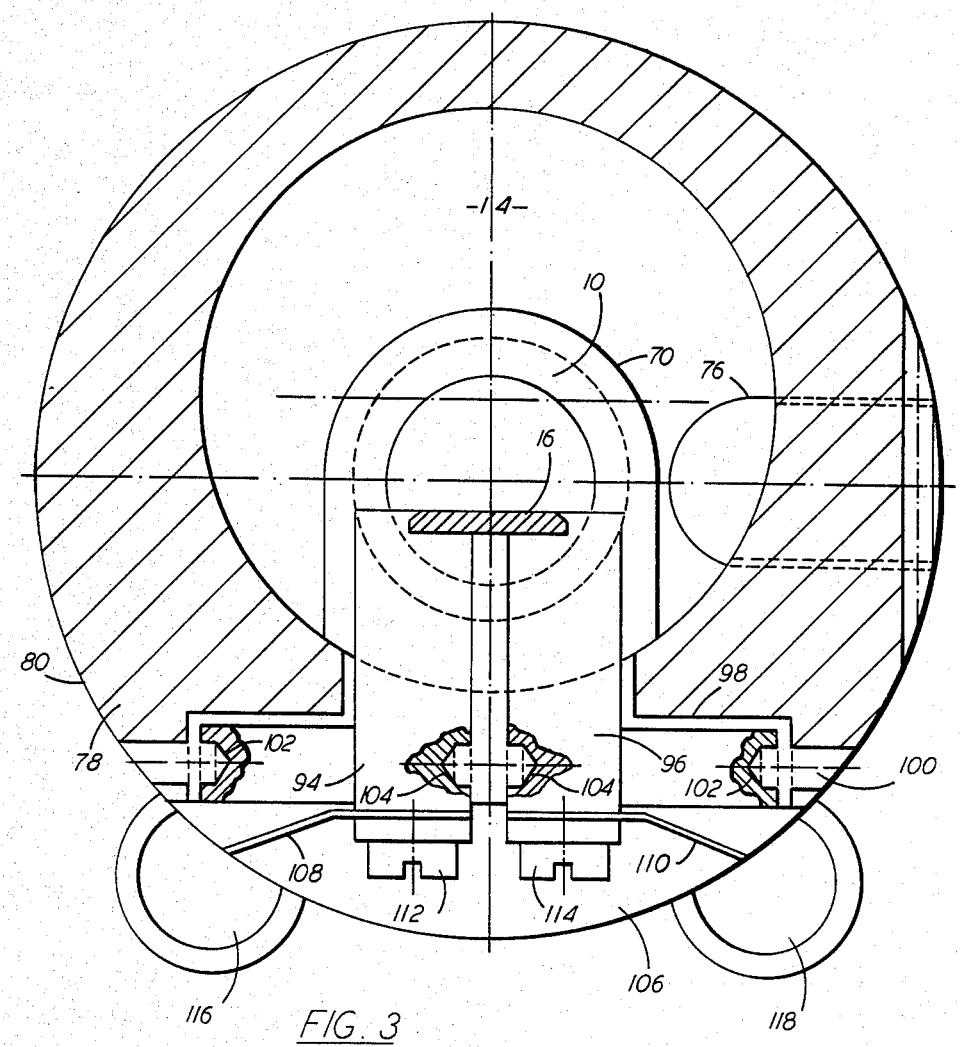
FIG. 3 is a partial cross-sectional view of the device.
Figure 4:
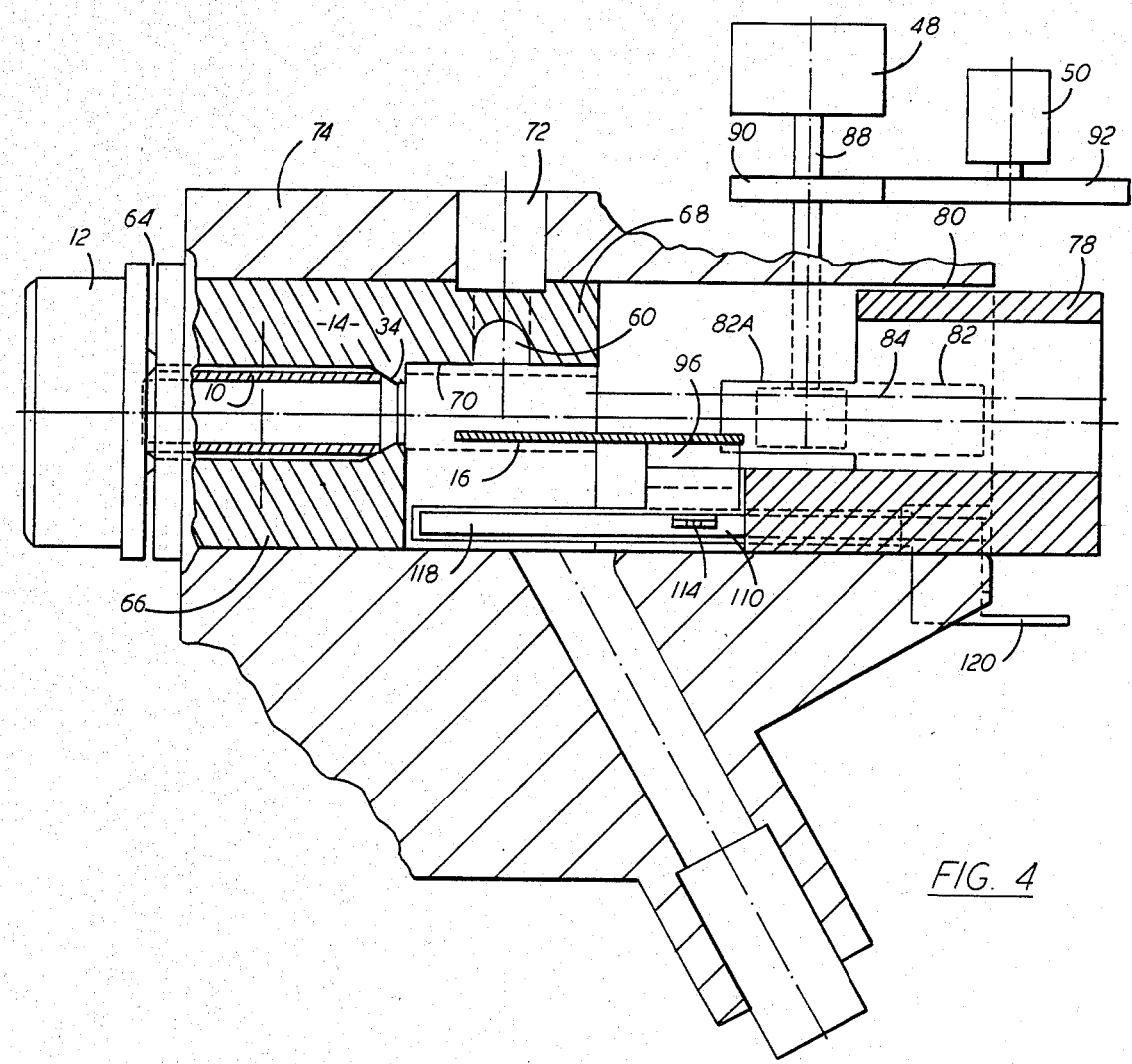
FIG. 4 is a partial longitudinal sectional view of the device.
Figure 6:
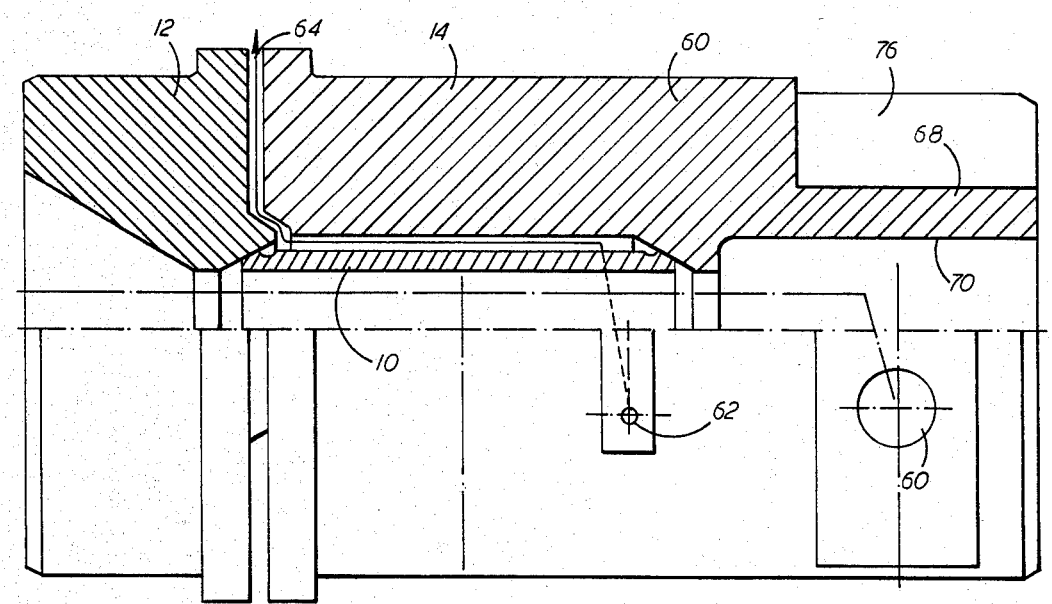
FIG. 6 shows electrodes, between which the graphite tube is mounted, at an enlarged scale.

As can be seen from FIGS. 3, 4 and 6, the electrode 14 includes a main portion 66 forming the contact face 34 and extending around the graphite tube 10 in the form of a jacket. An extension 68 is adjacent the main portion 66. The extension 68 has a U-shaped, tunnel-like recess 70 as clearly shown in FIG. 3. The dosing aperture 60 ends in the tunnel-like recess 70. An aperture 72 in a housing 74 is aligned with the dosing aperture 60, which housing surrounds the electrode 66. Another tunnel-like recess 76, displaced by 90° with respect to the tunnel-like recess 70, formed in the extension 68. The sample carrier 16 is mounted on an annular carriage 78 which is adjustably guided in a bore 80 of the housing 74 coaxial to the graphite tube 10. A toothed latch 82 is laterally seated at the carriage 78, which toothed latch continues in a rack 82A projecting over the front edge of the carriage 78. The toothed latch 82 engages a pinion 84 driven by a motor 48 through a shaft 88. A gear 90 is affixed to the shaft 88, which gear 90 engages a gear 92. The gear 92 drives the potentiometer 50 which serves as a position sensor (FIG. 1).

The sample carrier 16 is held between a pair of graphite contacts 94, 96, which are attached to the front end of the carriage 78. To this end, the carriage has a recess 98 on its left end face, in FIG. 4, into which recess the graphite contacts 94 and 96 are placed and in which they are fixedly cast by means of an isolating mass 100. Bores 102 and 104, into which the casting compound penetrates, ensure safe anchorage. A free space 106 is formed below the graphite contacts 94 and 96. Contact springs 108 and 110 are fixed to the lower ends of the graphite contacts 94 and 96 by means of screws 112 and 114, respectively.

Two busses 116 and 118 extend along the bore 80, which busses are connected to terminals 120.

Figure 5:
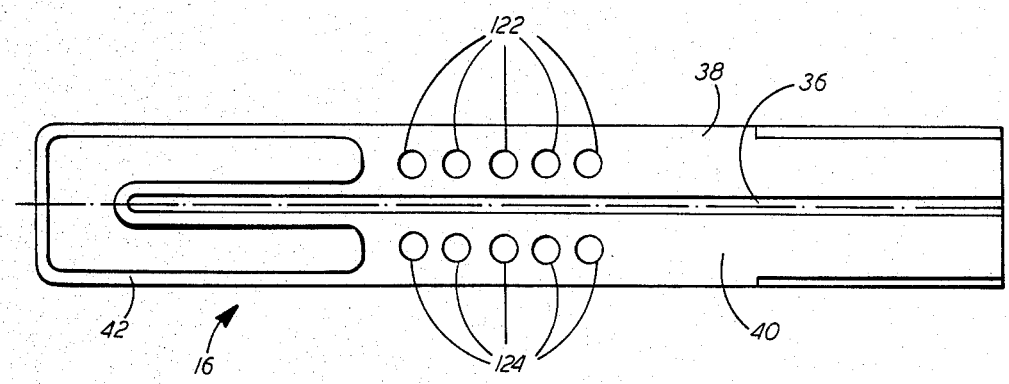
FIG. 5 shows an embodiment of an electrically heatable sample carrier.

The sample carrier 16 is illustrated at an enlarged scale in FIG. 5. The legs 38 and 40 each have a number of bores 122, 124, which are to reduce the heat dissipation. The terminals 120 are connected to the ends of the secondary winding 44 of the sample carrier transformer 28. Regardless of the position of the carriage 78 and the sample carrier 16, a current may be passed through the bus 116, the sliding contact 108, the graphite contact 94, the leg 40 of the sample carrier 16, the leg 38 of the sample carrier 16, the graphite contact 96, the sliding contact 110 and the bus 118. Consequently, directed electrical heating of the sample carrier 16 is possible in any position of the carriage 78.

As illustrated in FIG. 2, the sample carrier 16 may be moved alternately in one of three positions 122, 124 and 126. Position 122 is the inner position in which the cavity 42 of the sample carrier 16 is located in the middle of the graphite tube 10. In the position 124 shown in dashed lines in FIG. 2, the "dosing position", the cavity 42 is located below the dosing aperture 60. In this position of the sample carrier 16, sample may be applied through the dosing aperture 60. The sample may be applied by means of a device as illustrated, for example, in FIG. 3 of German Offenlegungsshrift No. 25 07 260. In the "outer position" 126, the sample carrier is located so far from the graphite tube 10 that its temperature is only slightly affected by the temperature of the graphite tube.

The program generator 18 has keys, by means of which a program can be preset. With the respective program step of the program generator 18, also the sample carrier control 52 is selected and the sample carrier is correspondingly moved into the inner, the dosing or the outer positions.

Figure 7:
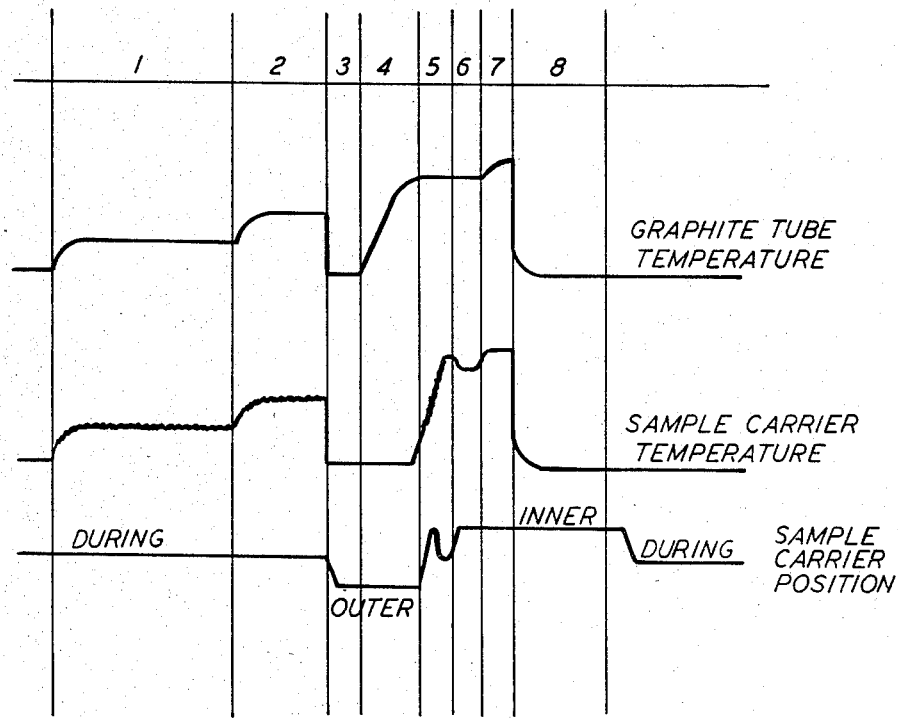
FIG. 7 illustrates a temperature program which can be executed with the device of FIGS. 1 to 6.

FIG. 7 shows a typical temperature program, as it is carried out with a device of the type described. During program step "1", the sample carrier 16 is in the dosing position 124. The graphite tube is pre-heated. Simultaneously, the sample carrier is heated actively, as indicated the cross-hatching of the curve "sample carrier temperature". In this program step, drying of the sample introduced through the dosing aperture 60 is effected. Vaporizing solvent is dissipated by the inner gas flow, as shown in FIG. 2. Subsequently, the thermal decomposition (ashing) of the sample is effected in the same position of the sample carrier 16. To this end, the temperature of both the graphite tube 10 and the sample carrier is further increased in step 2. The sample carrier remains in the dosing position 124. Smoke occuring during ashing is also dissipated by the inner gas flow through the dosing aperture 60. Thus, drying and ashing are effected outside the graphite tube by active heating of the sample carrier. The inner gas flow prevents vapors or decomposition products from entering the graphite tube. During the third program step, the temperature of both the graphite tube and the sample carrier 16 is decreased. The sample carrier 16 is moved into its outer position 126 (FIG. 2). During the next, i.e., fourth, step, the graphite tube 10 is heated up to atomizing temperature. The sample carrier remains at a distance from the graphite tube 10 at first such that its temperature is not yet affected by the graphite tube temperature. During the fifth program step, the sample carrier is advanced from position 126 into the inner position 122. Simultaneously, the sample carrier is actively heated, as indicated by the cross-hatching of the sample carrier temperature curve. Thereby, a rapid temperature increase of the sample carrier 16 is moved into the graphite tube 10 pre-heated up to atomizing temperature. Thereby, a narrow high peak occurs due to absorption of the measuring light beam in the resulting "cloud of atoms". The sample carrier is then retracted into the dosing position 124 for a short period of time and subsequently advanced into the graphite tube again, the heating of the sample carrier 16 being switched off. In this way, the graphite tube remains at its atomizing temperature during the sixth step. The temperature of the sample carrier 16 is slightly decreased relative to the maximum. The graphite tube is heated out in the next, i.e., seventh, step. The graphite tube temperature is further increased for a short period of time. Thus, the temperature of the sample carrier also increases. Thereby, residues of the sample which might have remained on the sample carrier or condensed on the graphite tube 10 are vaporized. The eighth step consists in cooling the graphite tube. The graphite tube temperature and the temperature of the sample carrier decrease after the heating has been switched off. Subsequently, the sample carrier is retracted into the dosing position 124.

The switch 46 is open during the phase where the graphite tube is heated but not the sample carrier, e.g., during step 4. The sample carrier is retracted into the outer position 126, when the graphite tube 10 is heated and this heating is not to affect the sample carrier such as is the case in step 4, too.

The temperature of the sample carrier 16 is measured by the sensor 54 supplying an actual value for a temperature control in the dosing position 124. The sensor 56 substantially supplies an actual value of the temperature of the sample carrier 16, when the sample carrier 16 is located in its inner position 122. In other cases, the sensor 56 detects the temperature of the graphite tube 10.

While the foregoing description is directed to an exemplary specific embodiment, other applications and modifications are possible which do not depart from the scope and spirit of the present invention. Thus, the present invention is deemed limited only by the appended claims and the reasonable interpretation thereof.

What is claimed is:

1. Device for atomizing a sample in flameless atomic absorption spectroscopy, said device comprising:
   a graphite tube held between a pair of annular electrodes;
   a controllable power supply arranged to generate a current through said electrodes and through said graphite tube;
   a carriage moveable in a longitudinal direction either into or out of said tube, said carriage being guided by guide means disposed so that a measuring light beam may pass through said tube;
   an electrically conducting sample carrier attached to said carriage and disposed below said measuring light beam;
   said guide means having busses engaged by sliding contacts of said carriage, which continuously electrically connect to terminals of said electrically conducting sample carrier whereby a heating current may be passed through said sample carrier in any position of said carriage to thereby permit controlling of the temperature of said sample carrier at any position thereof; and
   a controller for controlling said power supply to control the temperature of said tube and for controlling the current through said sample carrier to control the temperature of said sample carrier, both temperatures being adjusted in accordance with a predetermined program.

2. Device as claimed in claim 1 wherein:
   a first pyrometric sensor is provided which is directed upon said sample carrier in its position outside said graphite tube; and
   a second pyrometric sensor which is located lateral of said measuring light beam and which is directed at an angle into the inside of said graphite tube from the end face remote from said carriage.

3. Device as claimed in claim 2 wherein:
   the temperature signals from said sensors being applied to said power supply as actual value signals of a temperature program control; and
   said first or said second sensor is adapted to be connected with said power supply by means of a sensor selected switch.

4. Device as claimed in claim 2 wherein:
   said first pyrometric sensor is directed at an angle onto the lower side of said sample carrier.

5. Device as claimed in claim 1 wherein:
   said power supply contains a first transformer the secondary winding of which is connected to said annular electrodes such that said first transformer generates a heating current through said graphite tube;
   a second transformer the secondary winding of which is connected to said busses such that said second transformer generates a heating current through said sample carrier; and
   the primary windings of said two transformers are connected in parallel.

6. Device as claimed in claim 5 wherein:
   a switch is connected in series with said primary winding of said second transformer.

* * * * *